United States Patent [19]
Krone-Schmidt

[11] Patent Number: 5,777,726
[45] Date of Patent: Jul. 7, 1998

[54] SPECTROPHOTOMETRIC SUPERCRITICAL FLUID CONTAMINATION MONITOR

[75] Inventor: Wilfried Krone-Schmidt, Fullerton, Calif.

[73] Assignee: Raytheon Company, Lexington, Mass.

[21] Appl. No.: 881,941

[22] Filed: May 12, 1992

[51] Int. Cl.$^6$ .................................................. G01N 1/00
[52] U.S. Cl. .................................................. 356/38; 250/341
[58] Field of Search ............................. 422/73, 82.06; 356/38, 36; 250/341

[56] References Cited

U.S. PATENT DOCUMENTS

| | | | |
|---|---|---|---|
| 4,568,447 | 2/1986 | Pujado et al. | 208/177 |
| 4,608,344 | 8/1986 | Carter et al. | 436/34 |
| 4,818,710 | 4/1989 | Sutherland et al. | 436/527 |
| 5,068,040 | 11/1991 | Jackson | 210/748 |
| 5,082,629 | 1/1992 | Burgess, Jr. et al. | 356/128 X |
| 5,165,005 | 11/1992 | Klainer et al. | 356/128 X |
| 5,213,619 | 5/1993 | Jackson et al. | 134/1 |

FOREIGN PATENT DOCUMENTS

| | | |
|---|---|---|
| 410610 | 1/1991 | European Pat. Off. |
| 61-269063 | 11/1986 | Japan |
| 62-095102 | 5/1987 | Japan |
| WO9110122 | 7/1991 | WIPO |

OTHER PUBLICATIONS

Grandprie et al, "Thin Film Planar Waveguide Sensor for Liquid Phase Absorbance Measurements," *Analytical Chemistry*, vol. 62, No. 18, Sep. 15, 1990.

*Primary Examiner*—Robert J. Warden
*Assistant Examiner*—L. Dawson
*Attorney, Agent, or Firm*—Glenn H. Lenzen, Jr.; Leonard A. Alkov

[57] ABSTRACT

A system for detecting the presence of contaminants in a flowing stream of supercritical fluid. A sample stream is removed from a flowing stream of supercritical fluid and subjected to reduced pressure in a contaminant measurement zone. The supercritical fluid turns into gas at the reduced pressure with the contaminants remaining in a non-gaseous form. An attenuated total reflectance plate is used to spectrophotometrically detect the presence of the non-gaseous contaminants which deposit on the surface of the plate within the contaminant measurement zone. The system is useful for spectrophotometrically detecting the presence and identity of contaminants in supercritical fluids and is useful in monitoring both cleaning processes and extraction processes.

15 Claims, 1 Drawing Sheet

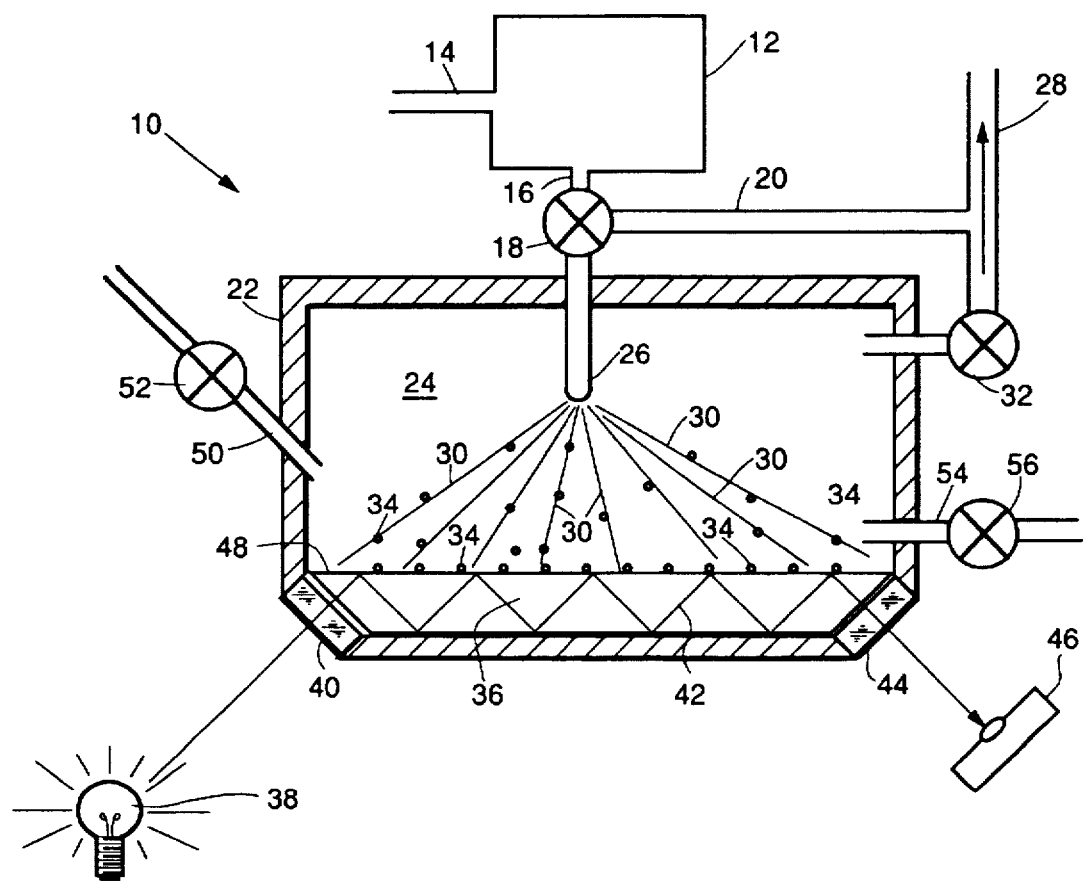

5,777,726

SPECTROPHOTOMETRIC SUPERCRITICAL FLUID CONTAMINATION MONITOR

BACKGROUND OF THE INVENTION

1. Field of the Invention

The present invention relates generally to the use of dense fluids for cleaning materials. More particularly, the present invention relates to spectrophotometrically detecting the presence of contaminants in such dense fluids and monitoring the amount of contaminants present in the dense fluids as the cleaning process progresses.

2. Description of Related Art

Conventional solvent-aided cleaning processes are currently under severe scrutiny due to problems with air pollution and ozone depletion. In addition, recent environmental concerns mandate that many of the organic solvents used in these processes be banned or their use severely limited. The use of dense phase gases for cleaning a wide variety of materials has been under investigation as an alternative to the above-mentioned solvent based cleaning processes. A dense phase gas is a gas compressed under either supercritical or subcritical conditions to liquid-like densities. These dense phase gases are also referred to as dense fluids. Unlike organic solvents, such as n-hexane, or 1,1,1-trichloromethane, dense phase gas solvents exhibit unique physical properties such as low surface tension, low viscosity, high diffusivity and variable solute carrying capacity.

The solvent properties of compressed gases are well known, as discussed in U.S. Pat. No. 5,068,040, assigned to the present assignee. In the late 1800's, Hannay and Hogarth found that inorganic salts could be dissolved in supercritical ethanol and ether (J. B. Hannay and H. Hogarth, *J.Prof.Rov-.Soc.* (London, 29, p.324, 1897). By the early 1900's, Buchner discovered that the solubility of organics such as naphthalene and phenols in supercritical carbon dioxide increased with pressure (E. A. Buchner, *Z.Physik.Chem.*, 54, p. 665, 1906). Within forty years Francis had established a large solubility database for liquified carbon dioxide which showed that many organic compounds were completely miscible (A. W. Francis, *J.Phys.Chem.*, 58, p. 1099, 1954).

In the 1960's there was much research and use of dense gases in the area of chromatography. Supercritical fluids (SCF) were used as the mobile phase in separating nonvolatile chemicals (S. R. Springston and M. Novotny, "Kinetic Optimization of Capillary Supercritical Chromatography using Carbon Dioxide as the Mobile Phase", *CHROMATOGRAPHIA*, Vol. 14, No. 12, p. 679, December 1981). Today the environmental risks and costs associated with conventional solvent-aided separation processes require industry to develop safer and more cost-effective alternatives.

The volume of current literature on solvent-aided separation processes using dense phase carbon dioxide as a solvent is evidence of the extent of industrial research and development in the field. Documented industrial applications utilizing dense fluid cleaning include extraction of oil from soybeans (J. P. Friedrich and G. R. List and A. J. Heakin, "Petroleum-Free Extracts of Oil from Soybeans", *JAOCS*, Vol. 59, No. 7, July 1982), decaffination of coffee (C. Grimmett, *Chem.Ind.*, Vol. 6, p. 228, 1981), extraction of pyridines from coal (T. G. Squires, et al., "Supercritical Solvents. Carbon Dioxide Extraction of Retained Pyridine from Pyridine Extracts of Coal", FUEL, Vol. 61, November 1982), extraction of flavorants from hops (R. Vollbrecht, "Extraction of Hops with Supercritical Carbon Dioxide", *Chemistry and Industry*, 19 Jun. 1982), and regenerating absorbents (activated carbon) (M. Modell, "Process for Regenerating Adsorbents with Supercritical Fluids", U.S. Pat. No. 4,124,528, issued 7 Nov. 1978).

Electro-optical devices, lasers and spacecraft assemblies are fabricated from many different types of materials having various internal/external geometrical structures which are generally contaminated with more than one type of contamination. These highly complex and delicate systems are generally classified together as "complex hardware". Conventional cleaning techniques for removing contamination from such complex hardware requires that the hardware be continually cleaned during assembly. The use of supercritical fluids, such as carbon dioxide is particularly well-suited for cleaning such complex hardware.

Supercritical fluid cleaning systems operate at high temperatures and pressures. As a result, real time monitoring of the cleaning process is difficult. In current systems, parts and materials are cleaned or extracted for a period of time and then removed and tested for cleanliness. If the part is still contaminated, it must be reintroduced into the system and recleaned. In order to avoid having to reclean numerous parts, the parts are typically left in the system much longer than necessary to insure adequate cleanliness. This, of course, results in a great deal of unnecessary cleaning, waste of time, and increased costs.

It would be desirable to provide a system for monitoring supercritical fluid cleaning systems to determine when the particular part has been completely cleaned or when the extraction of desired materials has been completed. Such a monitoring system should be simple, efficient and capable of being used to detect a wide variety of contaminants and to monitor a wide variety of cleaning/extraction processes utilizing supercritical fluids.

Minor changes in process parameters can affect the quality of a cleaning or extraction procedure utilizing supercritical fluids. Accordingly, it would be desirable to provide a process for conveniently, quickly and easily measuring the effectiveness of a cleaning and/or extraction procedure. In this way, various process parameters may be rapidly altered to establish the optimum cleaning/extraction conditions. The use of a monitoring system to provide a real-time indication of the degree of cleanliness or extraction in a particular procedure will be helpful in optimizing such procedures.

SUMMARY OF THE INVENTION

In accordance with the present invention, it was discovered that an attenuated total reflectance plate may be utilized as part of a spectrophotometric system to provide accurate detection of contaminants and monitoring of supercritical fluid cleaning processes. Attenuated total reflectance (ATR) plates, when used in conjunction with different ranges of electromagnetic radiation (e.g. infra-red, visible, ultra-violet), are useful in detecting the presence of a wide variety of contaminants and in monitoring the supercritical fluid cleaning/extraction of a wide variety of materials.

The present invention is based upon a system for detecting and/or identifying contaminants present in supercritical fluid. The system can also be used to monitor the amount of contaminants present in a flowing stream of supercritical fluid. During supercritical fluid cleaning and/or extraction processes, the amount of material, i.e. contaminants, in the flowing stream of supercritical fluid gradually decreases as the process continues. As the amount of contaminants decreases, the change in the amount of contaminants also decreases. Accordingly, monitoring of the change in the amount of contaminants present in the flowing stream of supercritical fluid provides an accurate and reliable real-time indication of the degree of cleanliness or extraction of a particular material. In addition, measurement of the total amount of contaminants deposited on a surface, such as an ATR plate provides an accurate measure of the overall effectiveness of a given extraction or cleaning procedure.

As a feature of the present invention, a sample stream of supercritical fluid is removed from the main cleaning or extraction stream. The sample stream of supercritical fluid is introduced into a low pressure measurement zone where the fluid is converted into a gas and the contaminants remain in a non-gaseous form. An attenuated total reflection plate system is provided onto which the non-gaseous contaminants are deposited. The particular wavelength of electromagnetic radiation passed through the attenuated total reflectance plate system is selected to detect the contaminant of interest. This provides for the capability of measuring a wide variety of contaminants which absorb electromagnetic radiation at various different wavelengths.

As another feature of the present invention, a valve is provided for allowing selective introduction of the sample stream into the measurement zone. During the early stages of the cleaning or extraction process, the contaminant levels in the supercritical fluid may be high. Accordingly, the valve may be kept closed during the initial period to prevent the introduction of large amounts of contaminants into the measurement zone which build up on the attenuated total reflection plate. The valve remains closed until sufficient processing time has elapsed and contaminant levels in the supercritical fluid have reached sufficiently low levels. The use of a valve for selected introduction of supercritical fluid into the measurement zone allows one to extend the time between periodic cleaning of the attenuated total reflectance plate. As another feature of the present invention, the attenuated total reflectance plate is periodically cleaned by exposing it to a solvent such as heptane at ambient pressure within the measurement zone. As an alternate feature of the present invention, the attenuated total reflectance plate may be subjected to cleaning utilizing supercritical fluid either in the measurement zone or by removing the attenuated total reflectance plate and placing it in a cleaning chamber.

As another feature of the present invention, the total amount of contaminants deposited on the attenuated total reflectance plate may be measured during a particular cleaning process. This capability to quantitatively measure the amount of contaminants deposited on the plate allows one to adjust various process parameters to optimize a particular cleaning and/or extraction procedure.

The above-discussed and many other features and attendant advantages of the present invention will become better understood by reference to the following detailed description when taken in conjunction with the accompanying drawing.

BRIEF DESCRIPTION OF THE DRAWING

The FIGURE is a schematic representation of a preferred exemplary spectrophotometric supercritical fluid contamination monitor in accordance with the present invention.

DESCRIPTION OF THE PREFERRED EMBODIMENTS

The monitoring system in accordance with the present invention may be used to monitor contaminants present in a wide variety of supercritical fluids. The present invention is useful in monitoring both cleaning processes and extraction processes. The term "contaminants" is intended to cover both desirable and undesirable materials present in the supercritical fluid. For example, there may be instances in extraction processes when the material extracted into the supercritical fluid may be a desirable product which is isolated and recovered at a later time. For the purposes of this specification, such desirable materials present in the supercritical fluid will be classified and considered together with undesirable materials which are removed during a cleaning process and disposed of.

The following description will be limited to an exemplary system utilizing carbon dioxide as the supercritical fluid. It will be understood by those skilled in the art that the teachings set forth herein are applicable to any supercritical fluid system wherein the contaminants remain in a non-gaseous form when the supercritical fluid is converted to a gas at reduced pressures. In addition, the terms "supercritical fluid" as used herein is intended to include mixtures of fluids, such as primary supercritical fluid and a non-supercritical co-solvent which enhances cleaning or extracts contaminants which are insoluble in the primary supercritical fluid. The following description also will be limited to cleaning items to remove organic contaminants which are soluble in supercritical carbon dioxide fluid. However, it will also be understood that this system may be used for a variety of cleaning and/or extraction processes.

A preferred exemplary carbon dioxide supercritical fluid cleaning system is shown generally at 10 in the FIGURE. The system 10 includes a cleaning or extraction vessel 12 in which cleaning or extraction takes place. The temperature and pressure of the carbon dioxide supercritical fluid within the cleaning vessel 12 is maintained at desired levels required for the cleaning or extraction process. Typically, the temperature within vessel 12 will be on the order of 40° C. to 60° C. with the pressure being in the range of between about 1200 psi to 5000 psi (84 kg/cm$^2$ to 351 kg/cm$^2$).

The supercritical fluid carbon dioxide is introduced into the cleaning chamber 12 through inlet port 14 and exhausted through outlet port 16. The various pumps, temperature regulators, valves and other apparatus which are necessary to conduct supercritical fluid cleaning in chamber 12 are not shown in detail since these items are well known in the art.

Valve 18 is provided for controlling flow of supercritical cleaning fluid through outlet port 16. Valve 18 may be set so that all of the supercritical cleaning fluid is passed into chamber 22 through nozzle 26. When it is desired to by-pass the sampling chamber 22, valve 18 may be set so that all of the spent supercritical cleaning fluid is recycled through line 20 to line 28. Line 28 is connected to suitable separation equipment which removes contaminants and cleans the supercritical fluid for recycling back through line 14 into cleaning chamber 12. If desired, valve 18 may be set so that a portion of the supercritical fluid exiting through port 16 is passed to the sampling chamber 22 with the remaining portion being recycled directly through lines 20 and 28.

The supercritical cleaning fluid which enters measurement zone 24 through nozzle 26 expands into a gaseous form as represented by lines 30. Valve 32 is provided for controlling the flow of supercritical fluid (now in gaseous form) from the measurement zone 24 through recycle line 28. Valve 32 and any other associated pressure regulation equipment are set to maintain a pressure within measurement zone 24 which ensures that the supercritical cleaning fluid is converted to its gaseous phase. The pressure maintained within measurement zone 24 is preferably kept near atmospheric pressure. However, valve 32 may be set to higher pressure levels on the order of a few hundred psi (or about 14 to 21 Kg/cm$^2$) provided that the pressure remains below the level at which the supercritical fluid which enters through nozzle 26 is converted to gas.

The contaminants present in the supercritical fluid are separated from the fluid as it turns into the gaseous form in measurement zone 24. The contaminants, as represented by droplets 34, separate from the now gaseous supercritical fluid and deposit onto surface 48 of an attenuated total reflectance plate (ATR) 36. Surface 48 is the surface of the ATR which is exposed to the contents of the measurement zone 24. Since this surface 48 is external to the remainder of the ATR, it is referred to herein as external surface 48 of the ATR. Attenuated total reflectance plates are well known in the art of spectrophotometry and are commonly used in Fourier-transform infrared (IR), ultraviolet (UV), and visible spectrophotometers.

In accordance with the present invention, electromagnetic radiation is provided from source 38. The radiation is passed through window 40 and into the ATR plate 36. The angle at which the radiation is introduced into the ATR plate is selected so that the radiation remains within the ATR plate as represented by serrated line 42. The electromagnetic radiation interacts with the contaminants 34 present on the exterior surface 48 of the ATR plate. The principles upon which electromagnetic radiation is absorbed by contaminants on the surface of the ATR plate are well known in the art and will not be described in detail. The electromagnetic radiation, after interaction with contaminants 34 on the surface of the ATR plate 36, exits through window 44. The electromagnetic radiation which exits through window 44 is measured by detector 46.

As a feature of the present invention, wavelengths of electromagnetic radiation may be used even though they are strongly absorbed by carbon dioxide or other supercritical cleaning fluids. Since the electromagnetic radiation does not leave the ATR plate 36, the only absorption which occurs is due to interactions with contaminants present on the exterior surface 48 of the ATR plate. Accordingly, a wide variety of electromagnetic radiation wavelengths may be used depending upon the particular contaminant(s) being measured. The preferred wavelengths of electromagnetic radiation are in the ultraviolet, visible and infrared ranges. Wavelengths in this spectrum range from about 150 nanometers to 3000 nanometers.

During operation, a single wavelength may be passed through the ATR plate 36 in order to continually monitor the amount of contaminant being deposited on the plate surface 48 during a particular cleaning or extraction process. Alternatively, the wavelength of the electromagnetic radiation may be varied in order to obtain spectra of the contaminant(s) to allow identification. The well known principals of UV, visible, and infrared spectroscopy may be applied in accordance with the present invention to allow both quantitative and/or qualitative measurement of contaminants as they are deposited on the ATR exterior surface 48.

In accordance with the present invention, ultraviolet radiation may be used to spectroscopically detect and monitor organic contaminants present in the supercritical cleaning fluid. Such contaminants include trace amounts of organic and biological compounds such as carbamates, thioketones, and amines. Highly colored contaminants such as dyes may be monitored in accordance with the present invention preferably using visible light spectroscopy. Infrared radiation is preferably used to detect and identify a wide variety of organic inorganic, and organometallic contaminants.

The monitoring system in accordance with the present invention may be used to continually monitor a cleaning or extraction process to detect when the process is completed. When used in this way, the change in absorbance at a particular wavelength radiation is monitored to determine when the change in absorbance approaches zero. As a cleaning or extraction process approaches completion, the amount of contaminants exiting the cleaning chamber 12 also decreases. As a result, the total amount of contaminants deposited on the ATR exterior surface 48 reaches a maximum level and then remains constant. Utilizing the spectroscopic detection system in accordance with the present invention allows one to accurately determine when the deposition of contaminants on the ATR plate has reached a maximum.

The present invention may also be used to determine optimum cleaning conditions. In this embodiment, a series of cleaning and/or extraction procedures is carried out with minor variations in cleaning conditions being made. The total amount of contaminant or extractant is quantitatively measured using the spectroscopic system of the present invention to provide an accurate indication of which process parameters provide the optimum cleaning and/or extraction.

In order to provide accurate spectroscopic measurements, it is required that the exterior surface 48 of the ATR plate 36 be periodically cleaned. The ATR plate may be removed from the measurement zone 24 and cleaned using conventional cleaning solvents, such as heptane, methylethyl ketone or other suitable solvent designed to remove organic contaminants. Other suitable solvents and detergents are used depending upon the type of contaminants present in the supercritical cleaning fluid.

Preferably, the ATR plate 36 is left in place within the measurement or sampling chamber 22 during the cleaning operation. One procedure for cleaning the ATR plate 36 involves introducing a suitable cleaning fluid onto the plate 36 by way of line 50 as controlled by valve 52. During the cleaning operation, valve 18 is closed so that continuous operation of cleaning chamber 12 may be conducted with the supercritical fluid being directed through line 20 for recycling. The solvent entering the measurement zone through line 50 is used to wash the contaminants from the ATR plate. The spent cleaning solvent is removed from the measurement zone 24 through line 54 as controlled by valve 56.

An alternative cleaning procedure involves closing valve 32 and allowing the pressure within the measurement zone 24 to increase to a level at which the supercritical fluid becomes liquid. At this point, contaminants present on the ATR plate will become redissolved in the liquid. The contaminated supercritical fluid can then be removed either through line 54 or line 28 for clean-up and recycling back to the cleaning chamber.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A system for detecting the presence of contaminants in supercritical fluid, said system comprising:

a processing vessel which contains supercritical fluid;

sampling means for removing at least a portion of supercritical fluid from said processing vessel and introducing said portion as a sample stream of supercritical fluid into a vessel having walls defining a contaminant measurement zone;

pressure releasing means for maintaining the pressure within said measurement zone at or below the level required to convert said sample stream into a gas wherein said contaminants present in said sample stream remain in a non-gaseous form;

an attenuated total reflectance plate having an exterior surface located within said measurement zone wherein said non-gaseous contaminants deposit on said exterior surface, said attenuated total reflectance plate having an electromagnetic radiation inlet and an electromagnetic radiation outlet;

means for introducing electromagnetic radiation into said attenuated total reflectance plate at said inlet wherein said radiation introduced into said plate remains within said plate, but interacts with said contaminants present on said exterior surface of said plate to produce altered electromagnetic radiation which exits said plate at said outlet; and means for detecting said altered electromagnetic radiation as it exits said attenuated total reflectance plate at said outlet to thereby provide real-time detection of said contaminants present in said supercritical fluid.

2. A system for detecting the presence of contaminants in supercritical fluid according to claim 1 wherein said means for introducing electromagnetic radiation comprises means for introducing infrared electromagnetic radiation into said inlet of said attenuated total reflectance plate.

3. A system for detecting the presence of contaminants in supercritical fluid according to claim 1 wherein said means for introducing electromagnetic radiation comprises means for introducing visible electromagnetic radiation into said inlet of said attenuated total reflectance plate.

4. A system for detecting the presence of contaminants in supercritical fluid according to claim 1 wherein said means for introducing electromagnetic radiation comprises means for introducing ultra-violet electromagnetic radiation into said inlet of said attenuated total reflectance plate.

5. A system for detecting the presence of contaminants in supercritical fluid according to claim 1 wherein said sampling means includes a sampling valve operable between open and closed positions for controllably introducing said sample stream into said measurement zone.

6. A system for detecting the presence of contaminants in supercritical fluid according to claim 1 wherein said system further including means for periodically cleaning said contaminants from said exterior surface of said attenuated total reflectance plate.

7. A system for detecting the presence of contaminants in supercritical fluid according to claim 6 wherein said means for periodically cleaning said contaminants from said attenuated total reflectance plate comprises:

a cleaning fluid inlet in said vessel;

means for introducing cleaning fluid into contact with said exterior surface of said attenuated total reflectance plate to produce spent cleaning fluid containing said contaminants removed from said exterior surface; and means for removing said spent cleaning fluid from said vessel.

8. A system for detecting the presence of contaminants in supercritical fluid according to claim 6 wherein said means for periodically cleaning said contaminants from said attenuated total reflectance plate comprises:

means for contacting said attenuated total reflectance plate with supercritical fluid in said measurement zone to remove said contaminants therefrom to form contaminated supercritical fluid; and means for removing said contaminated supercritical fluid from said measurement zone.

9. A method for detecting the presence of contaminants in supercritical fluid comprising the steps of:

providing a processing vessel which contains supercritical fluid;

removing at least a portion of supercritical fluid from said processing vessel and introducing said portion of supercritical fluid into a contaminant measurement zone as a sample stream;

maintaining the pressure within said measurement zone at or below the level required to convert said sample stream into a gas wherein contaminants present in said sample stream remain in a non-gaseous form;

using an attenuated total reflectance plate to spectrophotometrically detect the presence of said non-gaseous contaminants which are deposited on the exterior surface of said plate to thereby provide for real-time detection of said contaminants present in said supercritical fluid.

10. A method for detecting the presence of contaminants in supercritical fluid according to claim 9 wherein infra-red electromagnetic radiation is introduced into said attenuated total reflectance plate for interaction with said contaminants present on said exterior surface of said plate to produce altered infra-red electromagnetic radiation and wherein said altered infra-red electromagnetic radiation is detected as it exits said attenuated total reflectance plate to thereby provide detection of said contaminants in said flowing stream of supercritical fluid.

11. A method for detecting the presence of contaminants in supercritical fluid according to claim 9 wherein visible electromagnetic radiation is introduced into said attenuated total reflectance plate for interaction with said contaminants present on the exterior surface of said plate to produce altered visible electromagnetic radiation and wherein said altered visible electromagnetic radiation is detected as it exits said attenuated total reflectance plate to thereby provide detection of said contaminants in said flowing stream of supercritical fluid.

12. A method for detecting the presence of contaminants in supercritical fluid according to claim 9 wherein ultra-violet electromagnetic radiation is introduced into said attenuated total reflectance plate for interaction with said contaminants present on the exterior surface of said plate to produce altered ultra-violet electromagnetic radiation and wherein said altered ultra-violet electromagnetic radiation is detected as it exits said attenuated total reflectance plate to thereby provide detection of said contaminants in said flowing stream of supercritical fluid.

13. A method for detecting the presence of contaminants in supercritical fluid according to claim 9 wherein said pressure in said measurement zone is maintained at approximately ambient pressure.

14. A method for detecting the presence of contaminants in supercritical fluid according to claim 9, said method further including the step of periodically cleaning said contaminants from said exterior surface of said attenuated total reflectance plate using supercritical fluid.

15. A method for detecting the presence of contaminants in supercritical fluid according to claim 9, said method further including the step of periodically cleaning said contaminants from said exterior surface of said attenuated total reflectance plate using a cleaning solvent.

* * * * *